United States Patent [19]

Dubner et al.

[11] Patent Number: 5,210,354

[45] Date of Patent: May 11, 1993

[54] PROPYLENE OXIDE-STYRENE MONOMER PROCESS

[75] Inventors: Walter S. Dubner, Wilmington, Del.; Robert N. Cochran, West Chester, Pa.

[73] Assignee: ARCO Chemical Technology, L.P., Wilmington, Del.

[21] Appl. No.: 880,836

[22] Filed: May 8, 1992

[51] Int. Cl.$^5$ .............................................. C07C 1/20
[52] U.S. Cl. .................................. 585/469; 585/905; 585/435; 585/437; 585/805
[58] Field of Search ............... 549/523, 524, 529, 512, 549/513; 585/905, 469, 805, 833, 435, 437, 807

[56] References Cited

U.S. PATENT DOCUMENTS

| | | | |
|---|---|---|---|
| 3,351,635 | 11/1967 | Kollar | 585/469 |
| 3,439,001 | 4/1969 | Pell et al. | |
| 3,819,663 | 6/1974 | Levine et al. | 549/529 |
| 4,066,706 | 1/1978 | Schmidt | |
| 4,093,636 | 6/1978 | Bost et al. | 549/529 |
| 4,262,143 | 4/1981 | Becker | |
| 4,375,570 | 3/1983 | Yudovich | 585/476 |

Primary Examiner—Olik Chaudhuri
Assistant Examiner—C. Everhart
Attorney, Agent, or Firm—William C. Long

[57] ABSTRACT

In the co-production oxide and styrene monomer, there is produced a sodium-containing heavy residue stream previously suitable only as a low grade fuel. In accordance with the invention, the heavy residue stream is contacted with aqueous acid, and the resulting mixture is phase separated into an aqueous sodium-containing phase and an organic phase reduced in sodium, and at least a portion of the organic phase reduced in sodium is converted to styrene monomer.

3 Claims, 1 Drawing Sheet

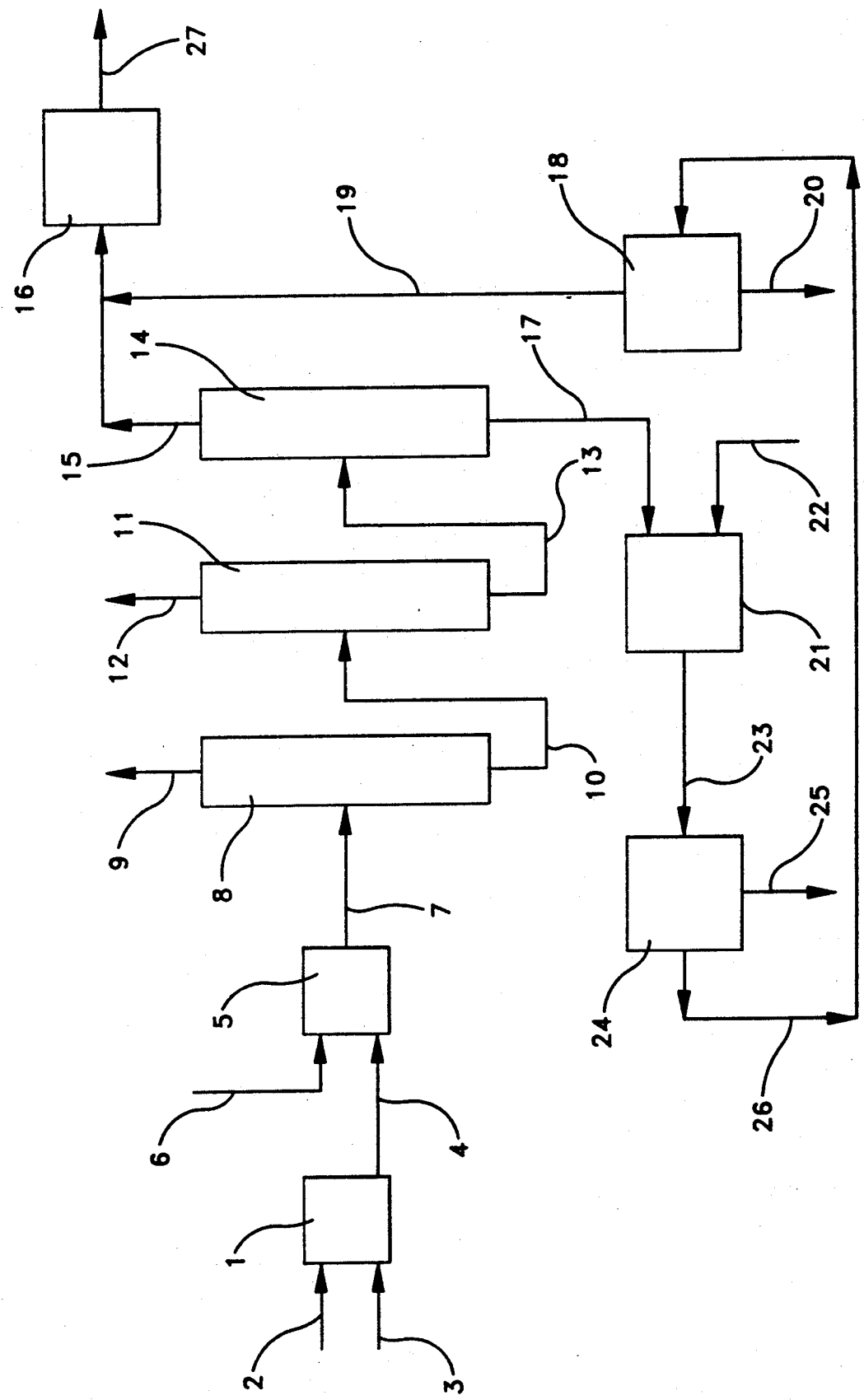

PROPYLENE OXIDE-STYRENE MONOMER PROCESS

BACKGROUND OF THE INVENTION

1. Field of the Invention

The present invention relates to an improved process for the co-production of propylene oxide and styrene monomer and especially to improved recovery of valuable 1-phenyl ethanol and styrene from heavy residual process streams by acid treatment and cracking.

2. Description of the Prior Art

An extremely successful process for the co-production of propylene oxide and styrene monomer involves the molecular oxygen oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to styrene monomer. The basic patent describing this process is U.S. Pat. No. 3,351,635.

In practice of the process, various distillation steps are employed in order to separate unreacted reagents as well as various product streams, and generally one or more caustic treatment steps are employed in order to reduce the acidic characteristics of various streams.

In commercial practice of the propylene oxide-styrene monomer process there is formed a heavy residue stream containing, as a result of one or more caustic treatments, relatively high levels of sodium compounds. Heretofore, such heavy residue has comprised a low value product stream suitable only for use as a low grade fuel.

BRIEF DESCRIPTION OF THE INVENTION

In accordance with the present invention, a process is provided whereby the low value product stream is upgraded and valuable products are recovered therefrom. The process of the invention involves treating the low value stream with aqueous acid and phase separating the resulting mixture into an aqueous phase containing most of the sodium previously associated with the low value stream and an organic stream phase having reduced sodium content. The resulting organic stream phase can be directly cracked at elevated temperature with the formation of 1-phenyl ethanol and styrene or the organic stream phase can be passed to a wiped film evaporator where a volatile stream is separated and cracked to form 1-phenyl ethanol and styrene, the heavy stream from the evaporator comprising a useful fuel.

DESCRIPTION OF THE DRAWING

The attached drawing illustrates in schematic form a practice of the invention.

DETAILED DESCRIPTION

In a first reaction step, ethyl benzene is reacted with molecular oxygen at elevated temperature in accordance with known techniques to form ethyl benzene hydroperoxide. U.S. Pat. No. 4,066,706 provides a comprehensive description of this reaction.

Suitably, a small amount of alkali is incorporated in the oxidation mixture as provided in U.S. Pat. No. 4,262,143 in order to improve oxidation rate and selectivity.

Ethyl benzene hydroperoxide is reacted with propylene to form propylene oxide and 1-phenyl ethanol. U.S. Pat. No. 3,351,635 describes suitable conditions and catalysts for this reaction.

The epoxidation reaction mixture is generally caustic washed and subjected to a series of distillations in order to separate materials contained therein. Generally, the reaction mixture is first distilled to separate unreacted propylene overhead from heavier components. The separated propylene is conveniently recycled to the epoxidation step.

The heavier components are then further distilled after caustic wash in a series of distillations to separate unreacted ethyl benzene which can be recycled, preferably after a caustic wash as described in U.S. Pat. No. 3,439,001, product propylene oxide, and product 1-phenyl ethanol leaving a heavy organic sodium-containing low value product stream.

The 1-phenyl ethanol stream is dehydrated to product styrene monomer in accordance with known procedures such as described in U.S. Pat. No. 3,351,635.

In accordance with the present invention, the sodium-containing low value organic product stream is treated in order to upgrade the stream and to recover valuable products therefrom.

In one embodiment, the low value product stream is thoroughly admixed with aqueous acid, preferably sulfuric acid, at relatively mild conditions, e.g. 20°–100° C., preferably 40°–90° C. The resulting mixture is separated into immiscible phases, specifically an aqueous sodium-containing phase and an organic phase having reduced sodium content.

The organic phase has added thereto a compatible acid catalyst such as p-toluene sulfonic acid and the resulting mixture is cracked at elevated temperature to form 1-phenyl ethanol and styrene monomer which products can be separated by distillation from remaining heavy materials. Conditions for the cracking include temperatures of 70° C. to 300° C., preferably 120° C. to 220° C. and pressures below atmospheric, eg. 100–400 m.m.Hg. which are appropriate for vaporization of light materials.

Product 1-phenyl ethanol and styrene monomer from the cracking represent increased yields of desired products o the overall process. Also, the heavy materials from the cracking are useful as fuel.

In another, more preferred practice of the invention, the organic phase from the acid treatment is subjected to a wiped film evaporation in order to separate up to about 40% by weight of the stream as volatile overhead fraction. It has been found that this overhead fraction can be passed directly to the 1-phenyl ethanol dehydration step employed in commercial propylene oxide/styrene monomer processes wherein components of the volatile overhead are converted to styrene monomer at the conditions conventionally employed for the 1-phenyl ethanol dehydration.

The heavy bottoms from the wiped film evaporation is, itself, useful as an upgraded fuel by virtue of the low sodium content thereof.

The acid employed in the heavy organic treatment is preferably sulfuric acid. Other less preferred acids are phosphoric acid, oxalic acid and the like.

The acid is used in at least an amount sufficient to react with all of the sodium in the heavy organic stream. In the case of sulfuric acid, sufficient acid is used to form sodium sulfate, i.e. 0.5 mol of sulfuric acid per mol of contained sodium, and preferably at least 1 mols sulfuric acid per mol of sodium are employed sufficient to form sodium bisulfate. Where other acids are used, equivalent amounts are employed.

The invention can be described with reference to accompanying FIG. 1 which is a schematic representation of a practice of the process.

Ethylbenzene is fed to reactor 1 via line 2 and therein oxidized to ethylbenzene hydroperoxide by reaction with molecular oxygen which is introduced via line 3. The reaction mixture from reactor 1 comprised of unreacted ethylbenzene, ethylbenzene hydroperoxide, 1-phenyl ethanol, acetophenone and heavies passes via line 4 to epoxidation reactor 5 wherein the ethylbenzene hydroperoxide is catalytically reacted with propylene introduced via line 6 to form propylene oxide.

The epoxidation reaction mixture is treated with aqueous caustic to neutralize acidic materials and to remove the epoxidation catalyst (not shown) and the treated epoxidation reaction mixture comprised of unreacted propylene, propylene oxide, ethylbenzene, 1-phenyl ethanol, acetophenone and heavy materials passes via line 7 to distillation zone 8. In distillation zone 8, an overhead mixture of unreacted propylene and product propylene oxide is separated via line 9. This mixture is subsequently resolved (not shown) into an unreacted propylene fraction for recycle and product propylene oxide which is further purified by conventional means.

A bottoms fraction comprised of ethyl benzene, 1-phenyl ethanol, acetophenone and heavies is removed from zone 8 via line 10 and passes to distillation zone 11. An overhead ethyl benzene stream is separated from zone 11 via line 12 and can be recycled to oxidation zone 1.

The bottoms stream from zone 11 comprised of 1-phenyl ethanol, acetophenone and heavies passes via line 13 to distillation zone 14. The overhead fraction from zone 14 comprised of 1-phenyl ethanol and acetophenone is separated via line 15 and passed to dehydration zone 16 wherein 1-phenyl ethanol is converted to styrene monomer which is recovered via line 27. Unreacted acetophenone is separated and passed to a hydrogenation zone (not shown) for conversion of acetophenone to 1-phenyl ethanol by known procedures, the 1-phenyl ethanol being recycled to zone 11.

The bottoms stream from zone 14 passes via line 17 to mixing zone 21 wherein it is mixed with aqueous sulfuric acid which is introduced via line 22.

The admixture from zone 21 passes via line 23 to decantation zone 24 wherein the immiscible phases are separated. The aqueous sodium-containing phase is separated by means of line 25 and may be further treated or discarded. The organic phase substantially reduced in sodium is removed via line 26 and passes to wiped film evaporator 18 wherein up to 40% by weight of the stream is separated as a distillate fraction via line 19. This fraction contains various 1-phenyl ethanol condensation products, some 1-phenyl ethanol, esters and the like. In this embodiment, the distillate fraction passes to dehydration zone 16 wherein components of the distillate are cracked and/or dehydrated to provide supplemental styrene monomer values. The heavy bottoms from wiped film evaporator 18 is recovered via line 20 and represents an upgraded stream suitable as heavy fuel.

EXAMPLE

The following example, which is described with reference to the accompanying drawing, illustrates the invention.

Ethylbenzene is introduced into zone 1 via line 2 at the rate of 2,680,000 lbs./hr. and therein is reacted with molecular oxygen introduced via line 3 at the rate of 50,000 lbs./hr. Also contained with the molecular oxygen are inerts, primarily nitrogen, in amount of 164,000 lbs./hr.

Oxidation conditions in reactor 1 are 135°–145° C. and 50–55 psig; residence time is 1.45 hr.

The liquid oxidation reaction mixture comprised by weight of about 59% ethylbenzene (EB), 35% ethylbenzene hydroperoxide (EBHP), 1.5% 1-phenyl ethanol (MBA), 2.8% acetophenone (ACP) and 1.7% others passes via line 4 at the rate of 467,000 lbs./hr. to epoxidation zone 5. Propylene is introduced into zone 5 via line 6 at the rate of 580,000 lbs./hr.

In zone 5 propylene is catalytically reacted with EBHP in the presence of 22 ppm as molybdenum of soluble molybdenum compound catalyst at 95°–115° C. and 600 psia, residence time being 1.7 hr.

The epoxidation reaction mixture passes from zone 5 via line 7 at the rate of 1,100,000 lbs./hr. and has a composition by weight of about 25% EB, 6% propylene oxide (PO), 48% propylene, 13% MBA, 2% ACP and 6% others. The epoxidation reaction mixture is treated with aqueous NaOH (not shown) to neutralize acidic materials and to remove the molybdenum catalyst. The treated mixture is decanted to separate an aqueous phase containing sodium and molybdenum compounds from the organic reaction mixture which contains about 100–150 ppm Na by weight. The mixture passes via line 7 to distillation zone 8 which actually represents a plurality of columns wherein various streams are separated by known means. Overhead components are removed via line 9 and comprises 60,000 lbs./hr. PO and 528,000 lbs./hr. propylene along with 43,000 lb./hr. of other light compounds which are treated by conventional means.

Bottoms from zone 8 passes at the rate of 490,000 lbs./hr. via line 10 to distillation zone 11.

The bottoms stream in line 10 has a weight composition of about 57% EB, 35% MBA, 5% ACP and 3% others. The total sodium content this stream is about 112–169 ppm.

Unreacted EB is distilled overhead at the rate of 280,000 lbs./hr. Bottoms from zone 11 is removed via line 13 at the rate of 204,000 lbs./hr. and comprises by weight about 83% MBA, 10% ACP and 7% others which are mainly oxygenated aryl compounds. This bottoms stream contains about 275–410 ppm by weight sodium.

The bottoms stream from zone 11 passes via line 13 to distillation zone 14 which actually comprises a plurality of separate columns. MBA and ACP are separated overhead by conventional means at the rate of 149,000 lbs./hr. The composition by weight of the overhead stream is about 87% MBA, 11% ACP and 2% others which are mainly oxygenated compounds.

A heavy bottoms stream is removed from zone 14 via line 17 at the rate of 7,000 lbs./hr. The heavies stream is primarily comprised of oxygenated aryl compounds with molecular weights greater than 225 g./mole and contains about 0.7 wt. % sodium. The heavy stream passes via line 17 to zone 21 wherein it is admixed with 1,000 lbs./hr. of 22 wt. % aqueous sulfuric acid introduced via line 22.

The mixture from zone 21 passes via line 23 to decantation zone 24 where the mixture is separated into aqueous and organic phases. An aqueous phase is separated via line 25 as a waste product stream containing 5.5 wt. % sodium.

The organic phase now containing only 40 ppm sodium passes at the rate of 7,100 lbs./hr. via line 26 to wiped film evaporator 18. From evaporator 18, a vapor stream is separated at 175° C. and 50 m.m.Hg. and passes therefrom at the rate of 2,200 lbs./hr. via line 19. A heavies stream containing 130 ppm sodium is recovered via line 20 at the rate of 4,900 lbs./hr. and comprises an upgraded heavy fuel.

The vapor mixture from wiped film evaporator 18 mainly comprises oxygenated aryl compounds including 1-phenyl ethanol ether, 1-phenyl ethanol, 1-phenyl ethanol and propylene oxide, condensation products, esters and the like. This mixture is combined with the MBA overhead from distillation column 14, and the combined streams from zones 14 and 18 are reacted in dehydration and cracking zone 16 at 200°-230° C. and 100-300 m.m.Hg. in the presence of 50-200 ppm para toluene sulfonic acid catalyst. The styrene-containing reaction mixture is recovered via line 27 at the rate of 16,900 lbs./hr. The composition by weight of this stream is about 80% styrene, 5% MBA, 11% ACP and 4% others, and styrene is recovered therefrom by conventional means.

Through practice of this invention, styrene production is increased by about 0.8% which in a world scale unit producing a billion pounds of styrene per year represents $2 million added value at current styrene prices. Additionally, the upgraded heavy fuel is of considerably greater value than the high sodium material produced by prior procedures.

What is claimed:

1. In a process for the co-production of propylene oxide and styrene monomer wherein ethylbenzene is oxidized to ethylbenzene hydroperoxide, said ethylbenzene hydroperoxide is reacted with propylene to form propylene oxide and 1-phenyl ethanol, unreacted propylene, propylene oxide and 1-phenyl ethanol are separately recovered by distillation leaving a heavy residue containing sodium and oxygen-containing organic materials formed in the process, and the 1-phenyl ethanol is dehydrated to styrene monomer, the improvement which comprises admixing the said heavy residue with aqueous acid, phase separating the resulting admixture into an aqueous sodium-containing phase and an organic phase having a reduced sodium content, and cracking at least a portion of the organic phase having a reduced sodium content to form styrene monomer.

2. The process of claim 1 wherein the said aqueous acid is aqueous sulfuric acid.

3. The process of claim 1 wherein said organic phase having a reduced sodium content is subjected to wiped film evaporation, up to 40 wt. % volatiles are separated and cracked to form styrene monomer.

* * * * *